(12) United States Patent
Bhatt et al.

(10) Patent No.: US 7,186,860 B2
(45) Date of Patent: Mar. 6, 2007

(54) PROCESS FOR THE PREPARATION OF 2-[(DIPHENYLMETHYL) THIO] ACETAMIDE

(75) Inventors: Surendra B. Bhatt, Vadodara (IN); Jiten R. Patel, Vadodara (IN); Dinesh Panchasara, Vadodara (IN); Hetal R. Shah, Vadodara (IN); Keshav Deo, Vadodara (IN); Vinod Kumar Kansal, Vadodara (IN)

(73) Assignee: Alembic Limited, Gujarat (IN)

( * ) Notice: Subject to any disclaimer, the term of this patent is extended or adjusted under 35 U.S.C. 154(b) by 0 days.

(21) Appl. No.: 10/543,748

(22) PCT Filed: Jan. 30, 2004

(86) PCT No.: PCT/IN2004/000033

§ 371 (c)(1),
(2), (4) Date: Feb. 28, 2006

(87) PCT Pub. No.: WO2004/075827

PCT Pub. Date: Sep. 10, 2004

(65) Prior Publication Data

US 2006/0128812 A1     Jun. 15, 2006

(30) Foreign Application Priority Data

Jan. 31, 2003 (IN) .................................. 130/03

(51) Int. Cl.
*C07C 323/29*    (2006.01)

(52) U.S. Cl. ........................................... 564/162
(58) Field of Classification Search ................. 564/162
See application file for complete search history.

(56) References Cited

U.S. PATENT DOCUMENTS

| 4,177,290 | A | 12/1979 | Lafon |
| 4,927,855 | A | 5/1990 | Lafon |
| 6,649,796 | B2 * | 11/2003 | Naddaka et al. ............ 564/162 |

FOREIGN PATENT DOCUMENTS

| EP | 0 233 106 | * | 8/1987 |
| GB | 1 520 812 | | 10/1975 |

* cited by examiner

*Primary Examiner*—Shailendra Kumar
(74) *Attorney, Agent, or Firm*—Hamre, Schumann, Mueller & Larson, PC

(57) ABSTRACT

Process for the preparation of 2-[(diphenylmethyl)thioacetamide, an intermediate for the preparation of Modafinil which is a CNS stimulant and used for the treatment of narcolepsia. The process comprises reacting 2-[(diphenylmethyl)thio] acetic acid with alcohols, in presence of catalytic amount of inorganic acid or organic acid at reflux temperature of alcohol to obtain corresponding ester which is reacted with ammonia to give 2-[(diphenylmethyl)thio]acetamide. If desired 2-[(diphenylmethyl)thioacetamide thus produced is reacted with hydrogen peroxide to produce Modafinil.

23 Claims, No Drawings

PROCESS FOR THE PREPARATION OF 2-[(DIPHENYLMETHYL) THIO] ACETAMIDE

This application is a 371 of PCT/IN04/00033, filed Jan. 30, 2004.

FIELD OF INVENTION

The present invention relates to a eco-friendly, high yielding and an improved process for preparing 2-[(diphenylmethyl)thio]acetamide (I), a key intermediate for the preparation of Modafinil {(±)2-[(diphenylmethyl)sulfinyl]acetamide} (II).

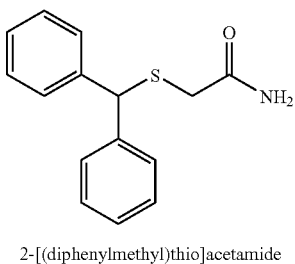

2-[(diphenylmethyl)thio]acetamide

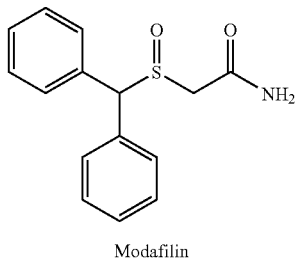

Modafilin

BACKGROUND OF THE INVENTION

The present invention relates to an improved, Eco friendly process for the preparation of 2-[(diphenylmethyl)thio]acetamide (I), a key intermediate for the manufacturing of Modafinil.

Modafinil is a CNS stimulant and is marketed under the trade name of "Provigil", for the treatment of narcolepsia. Lafon introduced Modafinil.

The preparation and pharmacological properties of Modafinil have been described in U.S. Pat. No. 4,177,290. U.S. Pat. No. 4,177,290 teaches two schemes (herein referred to as scheme 1 and scheme 2) for preparing Modafinil.

In scheme 1,2-[(diphenylmethyl)thio]acetic acid (III) is used as the starting material.

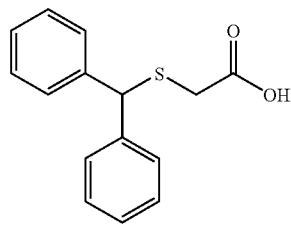

2-[(diphenylmethyl)thio]acetic acid

2-[(Diphenylmethyl)thio]acetic acid (III), on reaction with thionyl chloride yielded the corresponding 2-[(diphenylmethyl)thio]acetylchloride (IV), which on reaction with ammonia produced 2-[(diphenylmethyl)thio]acetamide (I) which on oxidation with hydrogen peroxide resulted in modafinil (II).

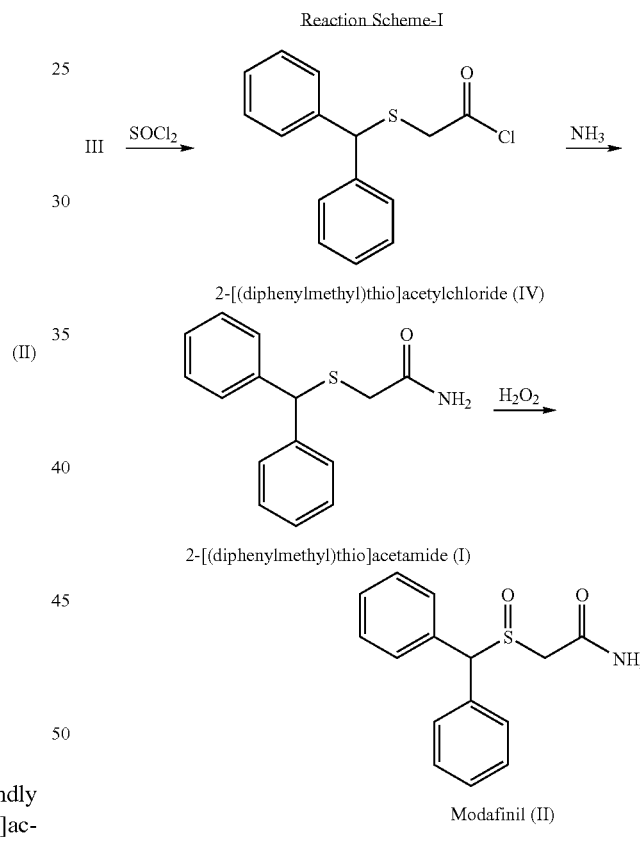

The aforesaid steps involve purification/separation of products in every step and the steps are not carried out in situ. In this scheme the yield of 2-[(diphenylmethyl)thio]acetamide (I) is stated to be 86% and that of Modafinil (II) as 73%.

Scheme 2 describes an industrial method for the preparation of Modafinil (II) wherein the all the reaction steps may be carried out in situ. In this scheme, the starting material is diphenylmethanol which is reacted with thiourea in the presence of HBr followed by basic hydrolysis and reaction with chloroacetic acid to form compound III. Hydrogen peroxide is then passed through the reaction mixture followed by acidification with hydrochloric acid to form (benzhydrylsulfinyl)acetic acid. The acid is reacted with dimethyl sulphate in presence of soda lye and sodium bicarbonate to obtain methyl(benzhydrylsulfinyl)acetate. After filtration methyl(benzhydrylsulfinyl)acetate is dissolved in methanol and ammonia is bubbled through the reaction mixture. After recrystallization and drying of the reaction mass Modafinil (II) is obtained with 41% total yield calculated from benzhydrol. The in-situ reaction scheme 2 is set out below.

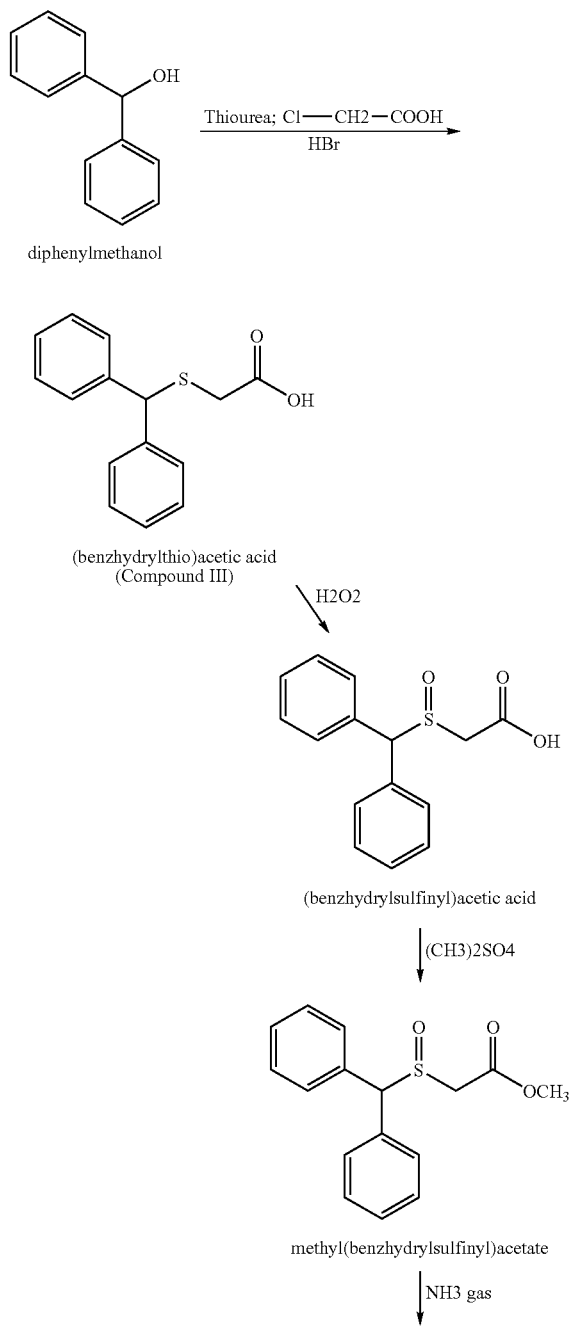

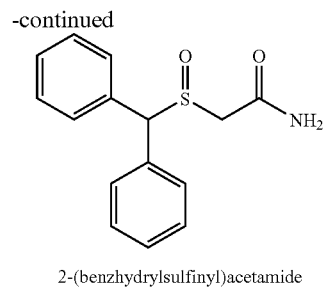

2-(benzhydrylsulfinyl)acetamide

The synthetic methods described in U.S. Pat. No. 4,177,290 have some inherent drawbacks. In scheme 1, the preparation of Modafinil involves three chemical steps with the yield in the final step being 73% and cumulative yield of Modafinil being 63%. The scheme does not involve reactions in-situ and require purification of products at the end of each step. Furthermore, thionyl chloride has been used for converting compound III to its acid chloride. Thionyl chloride is corrosive, hazardous, environmentally unfriendly and difficult to handle at commercial scale. Thus, the disclosed scheme is not suitable for industrial use. Moreover during the reaction, $SO_2$ and HCl are evolved as biproduct. To scrub out these gases, extra infrastructure is required. In addition to this, any leakage of these gases will lead to air pollution, which is injurious to the person living around and working in the plant.

With regard to scheme 2, the industrial method described therein gives very low yield of 41%. Moreover, the esterification of the sulphinyl acetic acid is carried out using dimethyl sulfate which is a well known hazardous reagent.

Thus there is a need for an improved process for the preparation of Modafinil to get higher yield-without the use of hazardous reagents.

OBJECTS OF THE INVENTION

It is therefore, an object of this invention is to provide a process for the preparation of 2-[(diphenylmethyl)thio]acetamide from thioaceticacid which would overcome the drawbacks and shortcomings of U.S. Pat. No. 4,177,290.

A further object of the invention is to provide a process that will eliminate the handling of all above hazardous reagents and to give higher yield and better quality of thioacetamide and Modafinil.

It is another object of the present invention to provide an in-situ method for preparing 2-[(diphenylmethyl)thio]acetamide from thioaceticacid which save the operation time and hence much more economical on commercial scale.

It is a still further object of the present invention to get Modafinil comprises only three chemical steps.

It is a still further object of the present invention that it does not utilize toxic or corrosive reagents, thus eco-friendly.

The applicants have now found that if compound III is first esterified to produce the corresponding thioacetate which in turn is reacted with ammonia to produce thioacetamide (I) and then converted to Modafinil (II) by reacting with hydrogen peroxide, the yield of Modafinil (II) is higher. It is also found that the step of esterification can be carried out with alcohol in presence of catalytic amounts of acid, thus avoiding use of dimethyl sulphate which is hazardous in nature.

SUMMARY OF THE INVENTION

Thus according to the present invention there is provided a process for the preparation of 2-[(diphenylmethyl)thioacetamide, a compound of formula (I) comprising reacting 2-[(diphenylmethyl)thio]acetic acid, a compound of formula (III) with alcohols, in presence of catalytic amount of inorganic acid or organic acid at reflux temperature of alcohol to obtain ester of formula (V) which is reacted with ammonia to give 2-[(diphenylmethyl)thio]acetamide of formula (I).

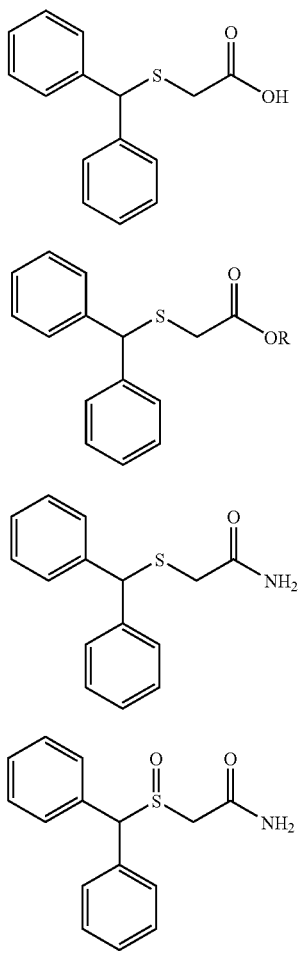

wherein R is an alkyl group with 1 to 6 carbon atoms and if desired 2-[(diphenylmethyl)thioacetamide thus produced is reacted with hydrogen peroxide to produce Modafinil, a compound of formula (II).

Ammonia is added to the ester in-situ or after isolating the ester from the reaction mixture.

The acid is selected from organic and inorganic acids. Preferred organic acids are alkyl or aromatic sulphonic acid, such as p-toluenesulphonic acid, methanesulphonic acid and its salts. Preferred inorganic acids are mineral acids, which are selected from Conc. $H_2SO_4$ and HCl.

DETAILED DESCRIPTION

According to the process of the present invention 2-[(diphenylmethyl)thio]acetic acid is reacted with different alcohol in presence of organic acids and mineral acids to produce ester of general formula (V). The ester either after isolation or in-situ is reacted with ammonia in presence of alcoholic solvents at temperatures ranging from 0–100° C. to produce 2-[(diphenylmethyl)thio]acetamide (I) in high yield and purity.

The alcohol, used in this invention is selected from alcohols with $C_1$ to $C_6$ alkyl group; preferably methanol, ethanol, n-propanol, and n-butanol.

Organic acids, used herein are alkyl or aromatic sulphonic acids, preferably p-toluene sulphonic acid or methane sulphonic acid and their derivatives.

Inorganic acids, used herein are mineral acid s, preferably conc. sulphuric acid or hydrochloric acid.

The temperature for the esterification is maintained in range of 30–90° C., preferably 60–90° C.

The ester is preferably reacted with alcoholic ammonia either in the same solvent or after evaporating to dryness in methanol to produce 2-[(diphenylmethyl)thio]acetamide (I).

The alcoholic ammonia is prepared by passing ammonia in alcohols. The preferred alcohols for preparing alcoholic ammonia are methanol or ethanol. The pressure of ammonia is preferably maintained at 0 to 6 kg, preferably 1.5 to 2 kg.

In the process of the present invention the ammonia is preferably purged into the reaction mixture of ester in alcohol.

The temperature during the preparation of 2-[(diphenylmethyl)]thioacetamide is maintained at 20–80° C. preferably 25–35° C.

According to a preferred aspect the present invention provides a process for the preparation of 2-[(diphenylmethyl)thio]acetamide comprising in-situ the reaction of 2-[(diphenylmethyl)thio]acetic acid with methanol in presence of either catalytic amount of conc. sulphuric or p-toluenesulphonic acid at 50–65° C. to give methylester which without isolation and then reacted with ammonia to furnish 2-[(diphenylmethyl)thio]acetamide (I).

According to another preferred aspect the present invention provides a process for the preparation of 2-[(diphenylmethyl)thio]acetamide, comprising reacting of the 2-[(diphenylmethyl)thio]acetic acid with ethanol in presence of catalytic amount of Conc. $H_2SO_4$ at reflux temperature to produce ethylester which without isolation is reacted with ammonia. Optionally ethanol is removed from the reaction mass and then the ester is reacted with methanolic ammonia.

According to another preferred aspect, 2-[(diphenylmethyl)thio]acetic acid is reacted in-situ with n-propanol in presence of catalytic amount of Conc. $H_2SO_4$ at reflux temperature to give n-propylester and then the generated ester is reacted with ammonia in methanol to get 2-[(diphenylmethyl)thio]acetamide.

According to another preferred aspect, 2-[(diphenylmethyl)thio]acetic acid is reacted in-situ with n-butanol in presence of catalytic amount of Conc. $H_2SO_4$ at reflux temperature to yield n-butylester and then the generated ester is reacted with ammonia in methanol to get 2-[(diphenylmethyl)thio]acetamide. 2-[(diphenylmethyl)thio]acetamide (I) thus prepared was converted to pure Modafinil having 94% yield and purity more than 99.5%. The cumilative yield from diphenyl methanol was found to be 67 to 73% as compared to 63%, as taught in U.S. Pat. No. 4,177,290.

All the physical properties and the NMR and IR spectra are in perfect agreement with the proposed structure.

The invention will now be described in connection with certain preferred embodiments in the following examples so that aspects there of may be more fully understood and appreciated, it is not intended to limit the invention to these particular embodiments.

EXAMPLE 1

Preparation of 2-[(diphenylmethyl)thio]acetamide

2-[(diphenylmethyl)thio]acetic acid (100 gm) was dissolved in methanol (500 ml) and sulphuric acid (20 ml) was added: The reaction mixture was refluxed till the end of reaction. The ester formation was checked on the TLC. After forming the complete ester, ammonia gas was bubbled at 1.5–2 kg pressure in reaction mass and stirred till the completion of the reaction. Water was added to reaction mixture. The precipitated solid was filtered off and dried to give 2-[(diphenylmethyl)thio]acetamide as a solid (90–95 g).

[HPLC Purity 95–98%, Yield 90–95%, M.P. 104–110° C.]1H-NMR (CDCl3); δ (ppm)=3.0(2H, s, CH2), 5.18 (1H, s, CH), 7.1–7.3(10H, m, Ar—H). 13C-NMR (CDCl3); δ(ppm)=36.0(CH2), 55.0 (CH); 128.0, 128.7, 129.2, 140.7 (Ph), 172.4 (C=O) IR (KBr): 3383 (—NH2); 1643 (CO str. —CONH2)

EXAMPLE 2

Preparation of 2-[(diphenylmethyl)thio]acetamide

2-[(diphenylmethyl)thio]acetic acid (5 g) was dissolved in Ethyl alcohol (25 ml) and sulphuric acid (1-ml) was added. The reaction mixture was refluxed till the end of the reaction. The ester formation was checked on the TLC. After forming the complete ester the excess alcohol was distilled out and methanol (25 ml) was added to the reaction mixture, ammonia gas was bubbled in the reaction mixture and stirring was carried out up to the completion of the reaction. The work-up as described in example-1 yielded 2-[(diphenylmethyl)thio]methylacetamide 4.5- to 4.7 g.

[HPLC Purity 98%, Yield 90–94%, M.P. 104–10° C.]

EXAMPLE 3

Preparation of 2-[(diphenylmethyl)thiol] acetamide

2-[(diphenylmethyl)thio]acetic acid (5 g) was dissolved in n-propyl alcohol (25-ml) and conc. sulphuric acid (1-ml) was added. The reaction mixture was refluxed till the end of the reaction. The ester formation was checked on the TLC. After completion of the reaction, the excess of n-propyl alcohol was distilled out and methanol (25 ml) was added to residue. Ammonia gas was bubbled in the reaction mass and stirred up to the completion of the reaction. The work-up as described in example-1 yielded 2-[(diphenylmethyl)thio]acetamide 4.5 to 4.7 g.

[HPLC Purity 97%, Yield 90–94%, M.P. 104–110° C.]

EXAMPLE 4

Preparation of 2-[(diphenylmethyl)thio]acetamide

2-[(diphenylmethyl)thio]acetic acid (5 gm) was dissolved in n-Butyl alcohol (25 ml) and sulphuric acid (1-ml) was added. The reaction mixture was refluxed till the end of the reaction. The ester formation was checked on the TLC. After forming the complete ester the excess of alcohol was distilled out. Methanol (25 ml) was added to residue. Ammonia gas was bubbled in the reaction mass and stirred up to the completion of the reaction. The work-up as described in example-1 yielded 2-[(diphenylmethyl)thio]acetamide 4.4–4.7 g.

[HPLC Purity 95%, Yield 90–94%, M.P. 104–110° C.]

EXAMPLE 5

Preparation of methyl 2-[(diphenylmethyl)thiol]-acetate

2-[(diphenylmethyl)thio]acetic acid (25 gm) was dissolved in methanol (125-ml) and sulphuric acid (5-ml) was added. The reaction mixture was refluxed till the end of reaction. The ester formation was checked on the TLC. After forming the complete ester, methanol was distilled out and pH was adjusted at 7.0–7.5 with Sodium bicarbonate and extraction was carried out with ethyl acetate. Ethyl acetate was distilled out completely under vacuum to give methyl 2-[(diphenylmethyl)thio]-acetate as an oil.

[HPLC Purity 99.77%, Yield 94–96%]1H-NMR (CDCl3); δ (ppm)=3.22(2H, s, CH2), 3.56 (3H, s, —CH3), 5.46 (1H, s, —CH), 7.22–7.5 (10H, m, Ar—H) IR (KBr): 1734 (-c=O Str.)

EXAMPLE 6

Preparation of 2-[(diphenylmethyl)thio]acetamide

Take methyl 2-[(diphenylmethyl)thio]acetate (5 g) in methanol (25 ml), bubbled ammonia gas in to the reaction mass and stir till the completion of the reaction. Isolate 2-[(diphenylmethyl)thio]acetamide as the solid product (4.4–4.5-g).

[HPLC Purity 99.7%, Yield 94–96%]

EXAMPLE 7

Preparation of Modafinil

Benzhydrylthioacetamide (100 gm) was dissolved in acetic acid (450 ml). H2O2 (44 ml) was added to this solution drop wise and the reaction mixture was heat around 30–35° C. till the completion of the reaction. The product was isolated by adding water in the reaction mixture and recrystallised with Methanol: water (4:1) to give Modafinil (100 g; 94%)

1H-NMR (CDCl3); δ (ppm)=3.19–3.39(2H, dd, CH2), 5.34 (1H, s, CH), 7.33–7.68(10H, m, Ar—H). 13C-NMR (CDCl3); δ(ppm)=56.9(—CH2), 69.7 (CH); 128.7, 129.3, 129.8, 130.5, 135.7, 137.9 (Ph), 167.2 (—CONH2) IR: 3313.5 (—NH2), 1685.9 (—C=O), 1033.4 (—S=O) M.P.: 162–164° C.

The invention claimed is:

1. Process for the preparation of 2-[(diphenylmethyl)thio] acetamide a compound of formula (I) comprising:
reacting 2-[(diphenylmethyl)thio]acetic acid, a compound of formula (III) with an alcohol, in the presence of a catalytic amount of inorganic acid or organic acid at a reflux temperature of the alcohol to obtain an ester of formula (V); and
reacting the ester of formula (V) with ammonia to give 2-[(diphenylmethyl)thio]acetamide

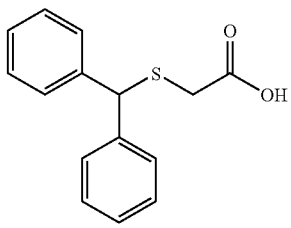

III

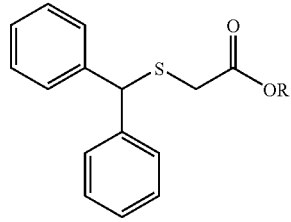

V

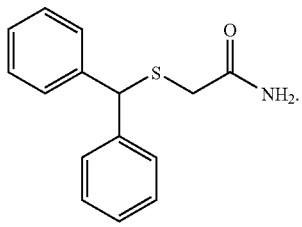

I

2. Process according to claim 1, wherein R is an alkyl group with 1 to 6 carbon atoms and further comprising reacting the 2-[(diphenylmethyl)thio]acetamide produced is oxidized to produce a compound of formula (II)

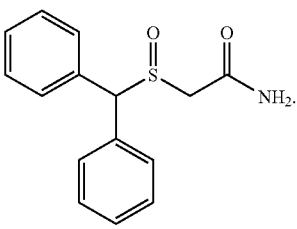

II

3. Process according to claim 1, wherein said ammonia is added to said ester in-situ.

4. Process according to claim 1, wherein said ammonia is added to said ester after isolating said ester from the reaction mixture.

5. Process according to claim 1, wherein said alcohol is selected from alcohols with alkyl groups with one to six carbon atoms.

6. Process according to claim 1, wherein said alcohol is selected from methanol, ethanol, n-propanol or n-butanol.

7. Process according to claim 1, wherein said alcohol is methanol.

8. Process according to claim 1, wherein said inorganic acid is selected from mineral acids.

9. Process according to claim 8, wherein said mineral acid is selected from conc. $H_2SO_4$ and HCl.

10. Process according to claim 1, wherein said organic acids are selected from alkyl and aryl sulphonic acids and their derivatives.

11. Process according to claim 10, wherein said sulphonic acids are selected from p-toluenesulphonicacid and methanesulphonic acid.

12. Process according to claim 1, wherein said ammonia is purged into a solution including the ester (V) in alcohol.

13. Process according claim 1, wherein said ammonia is alcoholic ammonia.

14. Process according to claim 13, wherein said alcoholic ammonia is prepared by passing ammonia through an alcohol before reaction.

15. Process according to claim 1, wherein the pressure of said ammonia is maintained at 0 to 6 kg.

16. Process according to claim 1 wherein, the temperature for preparing 2-[(diphenylmethyl)]thioacetamide is maintained at 20–80° C.

17. Process according to claim 1, wherein said alcohol is ethanol.

18. Process according to claim 13, wherein said alcoholic ammonia is prepared by passing ammonia through methanol before reaction.

19. Process according to claim 13, wherein said alcoholic ammonia is prepared by passing ammonia through ethanol before reaction.

20. Process according to claim 1, wherein the pressure of said ammonia is maintained at 1.5–2 kg.

21. Process according to claim 1, wherein the temperature for preparing 2-[(diphenylmethyl)]thioacetamide is maintained at 25–35° C.

22. Process according to claim 2, wherein the 2-[(diphenylmethyl)thio]acetamide produced is reacted with hydrogen peroxide to produce the compound of formula (II).

23. Process for the preparation of a compound of formula (II) comprising reacting 2-[(diphenylmethyl)thio]acetic acid, a compound of formula (III) with an alcohol, in the presence of a catalytic amount of inorganic acid or organic acid at a reflux temperature of alcohol to obtain ester of formula (V); and reacting the ester of formula V with alcoholic ammonia to give 2-[(diphenylmethyl)thio]acetamide, and oxidizing the 2-[(diphenylmethyl)thio]acetamide to produce the compound of formula (II)

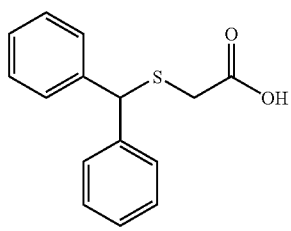

III

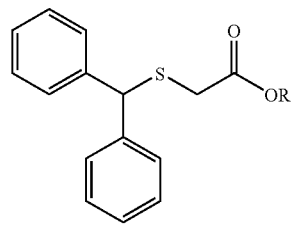

V

-continued
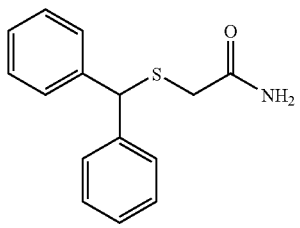
I
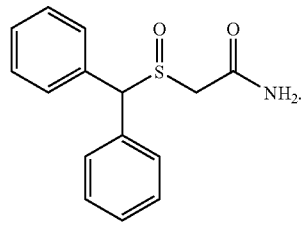
II
* * * * *